US010098715B2

(12) United States Patent
Joshi (10) Patent No.: US 10,098,715 B2
(45) Date of Patent: Oct. 16, 2018

(54) GENERATING A DESIGN FOR A DENTAL RESTORATIVE PRODUCT FROM DENTAL IMAGES

(71) Applicant: Dental Imaging Technologies Corporation, Hatfield, PA (US)

(72) Inventor: Sameer Anand Joshi, North Wales, PA (US)

(73) Assignee: DENTAl IMAGING TECHNOLOGIES CORPORATION, Hatfield, PA (US)

( * ) Notice: Subject to any disclaimer, the term of this patent is extended or adjusted under 35 U.S.C. 154(b) by 516 days.

(21) Appl. No.: 14/749,294

(22) Filed: Jun. 24, 2015

(65) Prior Publication Data

US 2016/0374784 A1 Dec. 29, 2016

(51) Int. Cl.
```
G06F 19/00      (2018.01)
A61C 13/00      (2006.01)
A61C 13/08      (2006.01)
A61B 5/055      (2006.01)
A61B 6/03       (2006.01)
A61B 6/14       (2006.01)
A61B 8/08       (2006.01)
```
(Continued)

(52) U.S. Cl.
CPC .......... *A61C 13/0013* (2013.01); *A61B 5/055* (2013.01); *A61B 6/032* (2013.01); *A61B 6/14* (2013.01); *A61B 8/08* (2013.01); *A61C 5/77* (2017.02); *A61C 9/0053* (2013.01); *A61C 13/0004* (2013.01); *A61C 13/08* (2013.01); *A61C 13/082* (2013.01); *B33Y 10/00* (2014.12)

(58) Field of Classification Search
CPC ........... A61B 5/055; A61B 6/032; A61B 6/14; A61B 8/08; A61C 13/0004; A61C 13/0013; A61C 13/08; A61C 13/082; A61C 5/77; A61C 9/0053; A61C 5/10; B33Y 10/00

See application file for complete search history.

(56) References Cited

U.S. PATENT DOCUMENTS 5,690,490 A   11/1997   Cannon et al.
8,255,071 B2  8/2012    Kaigler, Sr.
(Continued)

FOREIGN PATENT DOCUMENTS

GB   2373446 A   9/2002

OTHER PUBLICATIONS

Katsumata, Akitoshi, and Hiroshi Fujita. "Progress of computer-aided detection/diagnosis (CAD) in dentistry CAD in dentistry." Japanese Dental Science Review 50.3 (2014): 63-68.*

(Continued)

*Primary Examiner* — Michael D Masinick
(74) *Attorney, Agent, or Firm* — Michael Best & Friedrich LLP (57) ABSTRACT

Technology is described for generating a design for a dental restorative product from one or more dental images of a patient. The method can include obtaining a three-dimensional (3D) image of dentition of the patient prior to a change in dentition of the patient; and then determining the change in dentition of the patient. A design of a dental restorative product can be automatically generated for at least one tooth of the patient based on the 3D image of dentition prior to the change in dentition. Various other computer-implemented methods, systems, and computer-readable media are also disclosed.

20 Claims, 7 Drawing Sheets

(51) Int. Cl.
*A61C 9/00* (2006.01)
*A61C 5/77* (2017.01)
*B33Y 10/00* (2015.01)

(56) References Cited

U.S. PATENT DOCUMENTS

| | | | |
|---|---|---|---|
| 8,352,060 B2 | 1/2013 | Chun et al. | |
| 8,768,036 B2* | 7/2014 | Caligor | A61B 6/14 382/132 |
| 2006/0147872 A1* | 7/2006 | Andreiko | A61C 7/00 433/24 |
| 2008/0305458 A1 | 12/2008 | Lemchen | |
| 2009/0133260 A1 | 5/2009 | Durbin et al. | |
| 2012/0015330 A1 | 1/2012 | Zhivago | |
| 2012/0070802 A1 | 3/2012 | Woodward, III | |
| 2012/0100500 A1* | 4/2012 | Gao | A61C 1/084 433/72 |
| 2012/0261848 A1* | 10/2012 | Haraszati | A61C 13/0004 264/17 |
| 2013/0044932 A1* | 2/2013 | Caligor | A61B 6/14 382/132 |
| 2013/0108988 A1 | 5/2013 | Simoncic | |
| 2015/0165690 A1* | 6/2015 | Tow | B33Y 80/00 700/119 |
| 2016/0220200 A1* | 8/2016 | Sandholm | A61B 8/08 |

OTHER PUBLICATIONS

Rungruanganunt, Patchanee, J. Robert Kelly, and Douglas J. Adams. "Two imaging techniques for 3D quantification of pre-cementation space for CAD/CAM crowns." Journal of dentistry 38.12 (2010): 995-1000.*

Extended European Search Report from the European Patent Office for Application No. 16175869.3 dated Jan. 18, 2017 (9 pages).

Office Action from the European Patent Office for Application No. 16175869.3 dated Aug. 24, 2018 (4 pages).

* cited by examiner

GENERATING A DESIGN FOR A DENTAL RESTORATIVE PRODUCT FROM DENTAL IMAGES

FIELD OF THE INVENTION

Embodiments of the invention relate to manufacturing dental prosthetics. More particularly, embodiments of the invention relate to the capture and storage of dentition imagery for the design and fabrication of restorations (e.g., dental prosthetics) using three-dimensional (3D) printing and other manufacturing techniques.

BACKGROUND

Certain intra-oral imaging systems allow a dental practitioner to generate a 3D image of a patient's mouth and display the topographical characteristics of a tooth on a computer display monitor. The 3D image may take the form of a point cloud in a coordinate system fixed in 3D space. A surface may be fitted to this point cloud to generate a topographical map of the soft and hard tissue inside the patient's mouth. Intra-oral imaging devices can use various non-ionizing radiation (e.g., ordinary light and laser radiation) to create a point cloud or surface data of a patient's dentition.

Cone beam computed tomography (CBCT) involves the use of a rotating CBCT scanner gantry combined with algorithms or software on an image processing system to generate images of teeth and surrounding bone structure and soft tissue. The CBCT scanner uses high-energy radiation (e.g., x-ray radiation) to generate 3D imagery of the patient.

SUMMARY

In one embodiment, the invention provides a method for generating a design for a dental restorative product from one or more dental images of a patient. The method includes the step of obtaining a 3D image of dentition of the patient prior to a change in dentition of the patient. The step of determining the change in dentition of the patient follows. The next step of the method is automatically generating a design of a dental restorative product for at least one tooth of the patient based at least on the 3D image of dentition prior to the change in dentition. The automatic generation of the design of the dental restorative product uses a processor. The method may be executed as instructions on a machine, where the instructions are included on at least one computer readable medium or one non-transitory machine readable storage medium.

In one example, the step of determining the change in dentition of the patient includes obtaining a post-change 3D image of the patient after the change in dentition of the patient, and the generating step further includes generating the design based on at least one difference between the 3D image of dentition prior to the change in dentition and the post-change 3D image. The method can further include the step of fabricating the dental restorative product based on the design. The step of obtaining a 3D image of dentition of the patient is performed in a dental treatment office. The step of fabricating the dental restorative product can further include sending the design to a fabrication device, and fabricating the dental restorative product using the fabrication device based on the design. The fabrication device can include a milling machine or an additive manufacturing device located in the dental treatment office. The additive manufacturing device may use stereolithography, 3D printing, or digital-light-processing-based, 3D printing.

In another example, the step of obtaining a 3D image of dentition of the patient includes acquiring an image of dentition from an imaging device where the imaging device includes an intra-oral imaging device. Obtaining the 3D image of dentition may include using a non-ionizing scanner. The non-ionizing scanner may include an optical scanner or a laser scanner. The intra-oral image may include a stereolithography file or other type of surface geometry file. Alternatively, obtaining a 3D image of a patient may include acquiring a volumetric dental image of the patient using x-ray imaging, including but not limited to CBCT, other types of computed tomography (CT), volumetric tomography (VT), or any other suitable volumetric imaging method known in the art. Images may be obtained using other techniques or modalities including, for example, magnetic resonance imaging (MRI) or ultrasound imaging.

In still another example, the step of obtaining the 3D image of dentition of the patient further includes (1) acquiring an intra-oral image of the patient using a non-ionizing scanner; (2) determining a crown surface for a tooth above a periodontium based on the intra-oral image; (3) acquiring a volumetric dental image of the patient using an x-ray-based technology; (4) determining a geometry of tooth tissue for the tooth including at least a portion of root tissue surrounded by the periodontium based on the volumetric dental image; and (5) generating the 3D image of dentition including the crown surface and at least a portion of the root tissue based on a combination of the intra-oral image and the volumetric dental image using an iterative closest point (ICP) process or a 4 point congruent set (4PCS) process.

The design can include a computer-aided design-format (CAD-format) file or an image file. The dental restorative product can include a dental prosthesis, a denture, an implant, an inlay, a filling, a plug, a crown, an onlay, or a veneer. In another example, the method can further include the step of storing, in a data storage device, the 3D image of dentition of the patient prior to the change in dentition in a personalized library associated with the patient.

In another example, the method includes segmenting the 3D image of dentition of the patient to generate crown data of a tooth; processing the crown data to generate a crown design file; and storing the crown design file in a personalized library associated with the patient. In one configuration, the step of generating the design of the dental restorative product for at least one tooth of the patient includes obtaining the crown design file from the personalized library; and generating the design of the dental restorative product based on the crown design file. In another configuration, the step of obtaining 3D image of dentition of the patient further includes obtaining a pre-trauma design file previously saved in a personalized library of a data storage device prior to damage occurring to a tooth. The step of determining the change in dentition of the patient further includes obtaining a post-trauma design file saved in the personalized library after damage has occurred to the tooth.

The step of generating the design of the dental restorative product for the patient's tooth further includes comparing the pre-trauma design file and the post-trauma design file for the tooth. A dental restorative product file is generated based on a comparison between the pre-trauma design file and the post-trauma design file. The dental restorative product file may include tooth tissue present in the pre-trauma design file but missing in the post-trauma design file. In another configuration, the step of segmenting the 3D image of dentition of the patient further includes differentiating between tooth tissue and non-tooth tissue in the 3D image of dentition; and generating the crown data of the tooth based on the tooth tissue in the 3D image of dentition.

In another example, the method can further include the step of preparing a tooth for restoration after the step of obtaining a three-dimensional image of dentition of the patient prior to the change in dentition and before the step of determining the change in dentition. The step of preparing the tooth for restoration causes the change in dentition. The step of determining the change in dentition further includes obtaining a post-change 3D image of the patient.

In another embodiment the invention provides a dental computer-aided design (CAD) system having computing circuitry (e.g., processor or controller) configured to generate a design for a dental restorative product from one or more dental images of a patient. The computing circuitry is configured to obtain a 3D image of dentition of the patient prior to a change in dentition of the patient; determine the change in dentition of the patient; and automatically generate a design of a dental restorative product for at least one tooth of the patient based on the change in dentition of the patient and the 3D image of dentition prior to the change in dentition.

In one example, the computing circuitry is configured to implement the methods previously described. For example, the computing circuitry can be configured to obtain a post-change 3D image of the patient after the change in dentition of the patient, and generate the design based on at least one difference between the 3D image of dentition prior to the change in dentition and the post-change 3D image. The computing circuitry can be further configured to fabricate the dental restorative product based on the design. In another example, the computing circuitry is further configured to acquire the 3D image of dentition from an imaging device comprising an intra-oral imaging device or a volumetric dental imaging device.

In another embodiment the invention provides a system operable to generate a design for a dental restorative product from one or more dental images of a patient. The system can include an imaging module and a design module. The imaging module can be configured to generate and/or obtain a 3D image of dentition of the patient prior to a change in dentition of the patient. The design module can be configured to determine the change in dentition of the patient, and automatically generate a design of a dental restorative product for at least one tooth of the patient based on the change in dentition of the patient and the 3D image of dentition prior to the change in dentition.

In an example, the system can be configured to implement the method previously described. For example, the imaging module can be further configured to obtain an post-change 3D image of the patient after the change in dentition of the patient, and the design module can be further configured to generate the design based on at least one difference between the 3D image of dentition prior to the change in dentition and the post-change 3D image. In another example, the system includes a fabrication device to fabricate the dental restorative product based on the design. The fabrication device can include a milling machine or an additive manufacturing device. In another example, the system includes an image acquisition device to acquire or generate the 3D image of dentition. The imaging device can include an intra-oral imaging device or a volumetric dental imaging device. In another configuration, the system includes a storage device (e.g., volatile or non-volatile memory) to store the 3D image of dentition of the patient prior to the change in dentition in a personalized library associated with the patient.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. The same reference numerals in different drawings represent the same element. Numbers provided in flow charts and processes are provided for clarity in illustrating steps and operations and do not necessarily indicate a particular order or sequence.

Embodiments of the invention relate, among other things, to a method and system for the capture and storage of patient dentition intra-oral imagery and the use of those images in 3D computer-aided design and computer-aided manufacturing (CAD/CAM) systems for rapid design and fabrication of dental restorative product (e.g., a dental prosthesis) using 3D printing or additive manufacturing. Embodiments of the invention also relate to a fused intra-oral scan and CBCT imagery for integrated implant planning and restoration design. Dentition pertains to teeth and their arrangement in the mouth.

Combining a restoration design system (including software) with an intra-oral optical scanner allows a dental practitioner to design various types of restorations, including but not limited to dental prostheses, dentures, implants, inlays, fillings, plugs, onlays, crowns, and veneers. A dental prosthesis is used to restore (e.g., reconstruct) intraoral defects, including but not limited to missing teeth, missing parts of teeth, and missing soft or hard structures of the jaw and palate. Dentures (also referred to as false teeth) are prosthetic devices constructed to replace missing teeth. Dentures are supported by the surrounding soft and hard tissues of the oral cavity (i.e., mouth). A dental implant is a surgical component that interfaces with the bone of the jaw or skull to support a dental prosthesis, including but not limited to a crown, bridge, denture, facial prosthesis; or to act as an orthodontic anchor. An inlay is an indirect restoration (e.g., a filling) that includes a solid substance (e.g., metal, porcelain, or a cured composite resin) shaped to fit a cavity in a tooth and this is cemented into place. A dental filling is a dental restorative material used to restore the function, integrity, and morphology of missing tooth structure. Plug (e.g., collagen plug) is a material that can be used to fill a socket (e.g., hole) in a jawbone (e.g., when a tooth is extracted). An onlay is similar to an inlay, except that an onlay incorporates a replacement for a tooth cusp by covering the area where the missing cusp would be. Crowns (as a dental prosthetic device) are a type of onlay that completely covers surfaces of a tooth. A veneer is a thin layer of material placed over a tooth to improve the aesthetics of a tooth or to protect the surface of the tooth from damage.

As a first step in the restoration design process, a dental practitioner uses an intra-oral imaging device (112 of FIG. 1; e.g., optical scanner) to acquire an image of the patient's dentition from which a digital imprint or digital model of the patient's dentition can be made. Digital intra-oral imaging devices allow for storage of the scan data in a digital format (e.g., an open STL format or a proprietary format). STL (STereoLithography) is a file format native to stereolithography CAD software created by 3D Systems. However, other kinds of surface geometry file formats can be used. The digital data is then imported into 3D CAD software. The digital data provides the basic structure from which the dental practitioner can design a case specific restorative prosthesis. The 3D CAD software system can include various libraries of crown or tooth designs which are classified based upon position, age, or gender. CEREC (Chairside Economical Restoration of Esthetic Ceramics or CEramic REConstruction) and Compass are some examples of commercial 3D CAD software that utilize crown and tooth design image libraries. The crown can refer to the anatomical area of a tooth above the periodontium. The crown is usually covered by enamel. Periodontium refers to the specialized tissues that surround and support the teeth, which maintain the teeth in the maxillary and mandibular (jaw) bones.

Based upon an analysis of the patient's dentition, a stock design from the library can be recommended and selected by the software system as a starting point or the stock design can be manually selected by the dental practitioner based upon their experience. This selected stock design from a library can then be modified via scaling, stretching, or similar operations, performed in the 3D CAD software, so as to modify the stock library model to fit the patient anatomy. The occlusal surface can be designed manually by the dental practitioner (using the tools provided in the 3D CAD software) or automatically by the software based upon a computer algorithm. The computer generated surfaces may not be optimal and may need to be modified by the dental practitioner to ensure form and function for a particular patient. The occlusal surface is the surface of a tooth that can make contact with other teeth, including but not limited to the contact made between upper (i.e., maxillary) and lower (i.e., mandibular) teeth.

The process of selecting a stock design, modifying that design for a restorative prosthesis, setting up the design of the restorative prosthesis for fabrication by a restorative specialist (e.g., dental practitioner or dentist) can take upward of 12 to 15 minutes to complete. During this time of designing the restorative prosthesis, the patient may have to wait (in the dental chair). Minimizing the design time of the restorative prosthesis can improve the workflow in a dental office and improve patient satisfaction with the dental procedure. Additionally, the computer-generated occlusal surface based on the stock design may not be a close match to the natural tooth anatomy of the patient causing some qualitative "bite feel" issues that may need to be corrected by the dental practitioner.

CAD/CAM systems can also use a fabrication device using a milling process or additive manufacturing process to fabricate the restorative prostheses. Such computer controlled milling machines and additive manufacturing devices can be expensive and require careful maintenance (e.g., having large maintenance costs). Additionally, the material blanks (e.g., gold, silver, porcelain, or resins) used for fabrication of the prosthesis can be relatively expensive, making the per dental prosthesis cost high for the dental practitioner, which cost is usually passed on to the patient.

Advances in additive manufacturing technologies (e.g., 3D printing) and biocompatible resin materials allow for the manufacture of complex shapes (e.g., dental prostheses). These fabrication processes (e.g., using relatively low cost, small size, desktop 3D printer machines) and materials (e.g., higher density resins) can be used for chairside fabrication of restorative prostheses using additive manufacturing technologies (e.g., 3D printing) that have sufficient strength to be used as a long-term temporary dental restorative product. Higher strength materials, which can be used for the manufacture of permanent restorative prostheses using additive manufacturing techniques, are also being developed. Due to the nature of additive manufacturing, minimal material loss occurs during the manufacturing process, which can potentially provide material cost advantage over the use of a milling technique for fabrication of the prosthetic device. Chairside fabrication refers to fabrication performed in a dental treatment office instead of a design for a dental restorative product being sent off-site to a dental laboratory for fabrication. Chairside fabrication can allow a dental practitioner to design and fabricate a dental restorative product during a treatment session (i.e., appointment).

Figure 1:
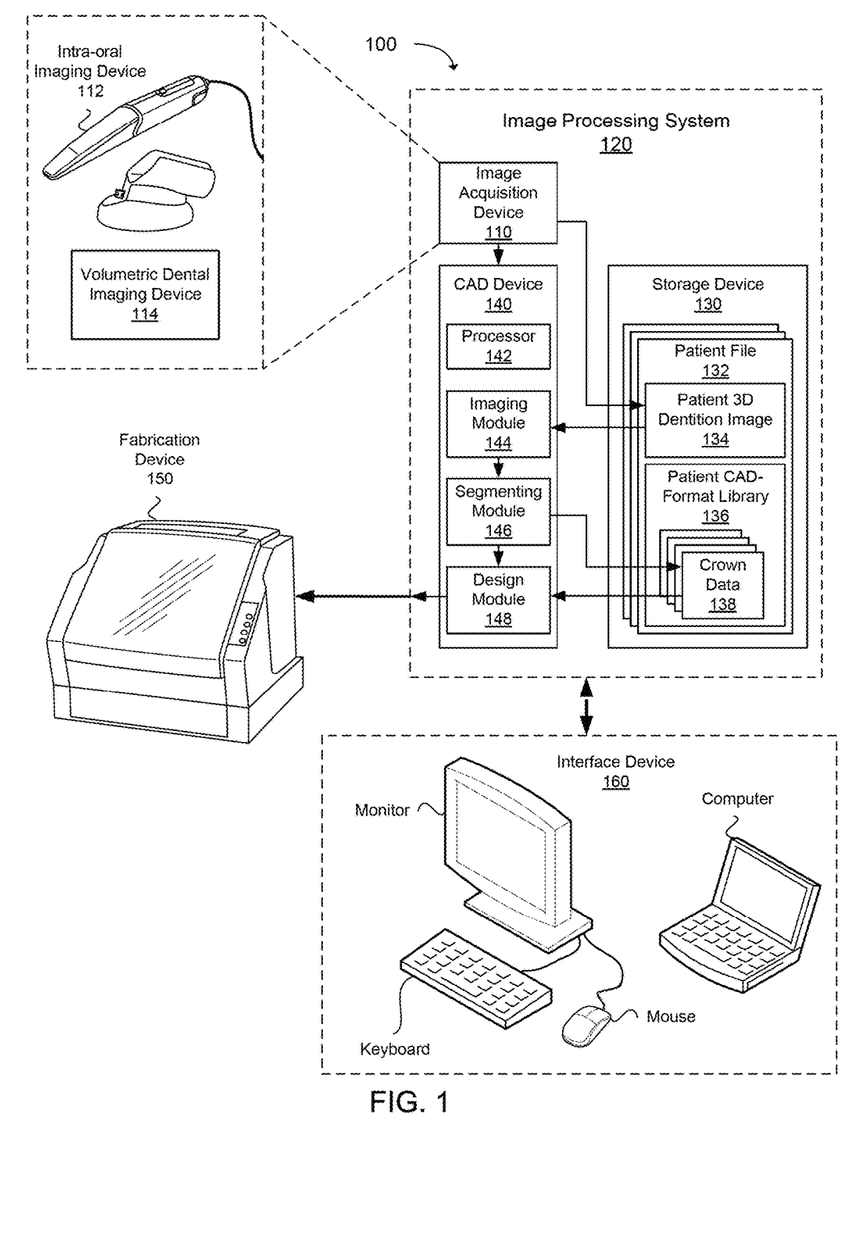
FIG. 1 illustrates a system to generate a design for a dental restorative product from a personalized library of one or more dental images of a patient using a segmentation module.

Instead of using stock designs from a CAD/CAM system library and modifying those designs in an attempt to match a patient's tooth profile to create a dental restorative product, the patient's own 3D images (e.g., optical imagery) can be used to automatically generate a design of a dental restorative product. As used in this disclosure, the term "automatic" or "automatically" refers to a process of generating a design based on an image of dentition without additional user input or commands. For example, FIG. 1 illustrates a restoration design and fabrication system 100 that can be used to design and fabricate a dental restorative product. The system 100 includes an image processing system 120, a fabrication device 150, and an interface device 160 (e.g., computer, laptop computer, monitor, keyboard, and/or mouse). The interface device 160 can be used by the dental practitioner to make selections, view the 3D images, manipulate and make changes to the design, and/or other functions related to the design and fabrication of the dental restorative product.

The image processing system 120 can include circuitry, software, computer hardware, components, and/or modules to generate a design for a dental restorative product. The image processing system 120 can also include or may be coupled to a fabrication device 150 (e.g., milling machine or additive manufacturing device) and/or an interface device 160, including but not limited to a computing device, an output device (e.g., monitor for displaying designs and images), and/or an input device (e.g., keyboard or mouse). In an example, the image processing system 120 along with the fabrication device 150 can be provided in a dental treatment office. In such situations, the image processing system 120 and the fabrication device 150 can be referred to as a chairside restoration design and fabrication system 100 or 200.

The image processing system 120 can include an image acquisition device 110, the storage device 130, and a CAD device 140. The image acquisition device 110 may be one of a number of different devices or two or more devices used in combination. In one example, the image acquisition device 110 includes an intra-oral imaging device 112 and/or a volumetric dental imaging device 114. Image data from the image acquisition device 110 is provided to the storage device 130 and/or the CAD device 140.

The storage device 130 can include one or more patient files 132. Each patient file includes one or more patient 3D dentition images 134 and/or a patient CAD-format library 136. The CAD format library 136 may include crown data 138 for one or more teeth. The storage device 130 can include volatile or non-volatile memory or storage elements, and can be either local to the dentist's office or remote (e.g., cloud storage).

The CAD device 140 can include a processor 142, an imaging module 144, a segmenting module 146, and a design module 148. The components of the restoration design and fabrication system 100, including the image processing system 120 and/or the fabrication device 150, are described in greater detail in relation to the design of the dental restorative product.

Figure 3A:
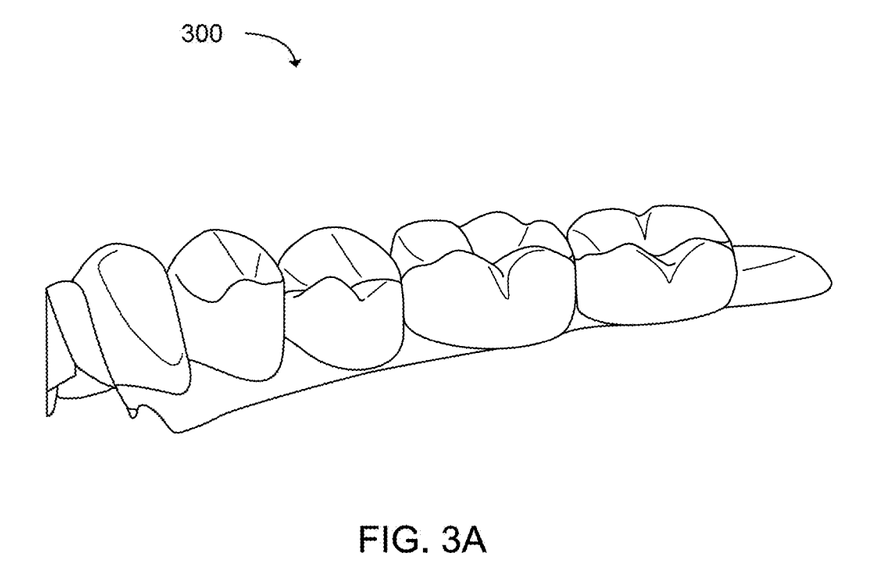
FIG. 3A illustrates intra-oral optical scan imagery including surface data and/or point cloud data.

To generate a design of a dental restorative product using a patient's own 3D images, the system 100 obtains the patient 3D images, for example, in advance of an event or trauma that causes a desire for the dental restorative product. For example, during a routine dental check-up (e.g., every five years as part of a full mouth series interval) the image acquisition device 110 is used to obtain 3D dentition images 134, which are then used to form a new (or update an existing) patient file 132 for storage in the storage device 130. FIG. 3A illustrates an intra-oral optical image, which is an example of a 3D dentition images 134.

Figure 3B:
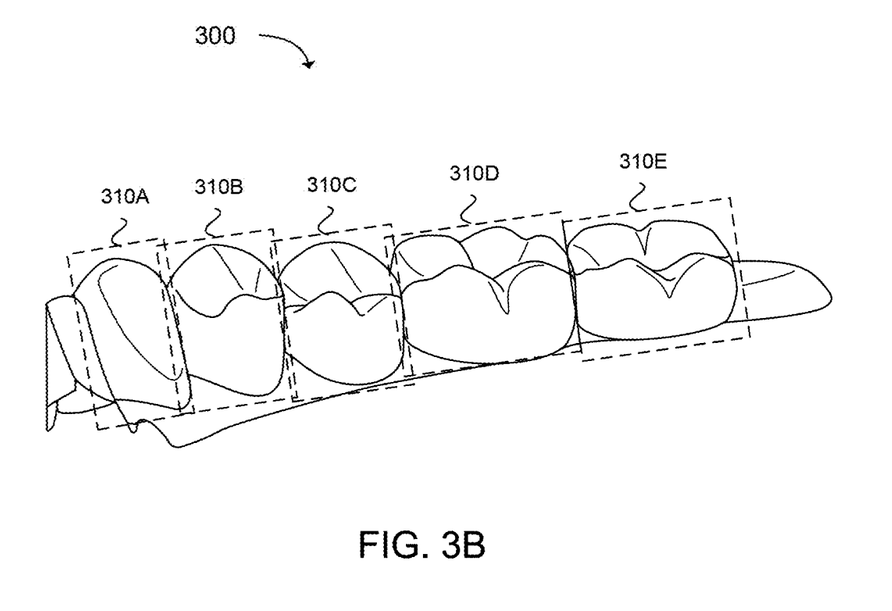
FIG. 3B illustrates segmented crown data overlaid on intra-oral optical scan imagery.

In some instances, the patient file 132 for a particular patient includes one or more 3D dentition images 134. In some instances, in addition to the 3D dentition images 134, the patient CAD-format library 136 is included in the patient file 132. To generate the patient CAD-format library 136, in some embodiments, the imaging module 144 obtains the patient 3D dentition images 134 from the patient file 132 or the image acquisition device 110. Then, the patient 3D dentition images 134 are segmented by a segmenting module 146 into individual crowns (310A-E of FIG. 3B) and stored in a digital format (e.g., CAD-format files or STL files) as crown data 138 files in the patient file 132. The set of digital formatted crown data 138 files can then provide a personalized anatomy library for the patient (e.g., patient CAD-format library 136), which can be used at some subsequent time as a template to generate a dental restorative product.

If and/or when the patient needs a restorative prosthesis constructed for a treatment option, a design module 148 of the image processing system 120 can recommend an initial design based on the patient's own personalized anatomy library (e.g., patient CAD-format library 136) or the dental practitioner can select the initial design from the patient's personalized anatomy library based on the tooth position. Such an initial design can be a very close match to the desired restorative prosthesis in terms of size, clearances, and occlusal surface design perspective since the initial design is based on the patient's dentition prior to a change in that dentition. As a result of the close match, the initial design may have less manipulation by the dental practitioner to generate a finalized design. The less manipulation can reduce the design time for the final restorative prosthesis and provide a better fit to the patient, as compared with the manipulation of a stock design or generic crown form fitted to the patient's anatomy.

Such an in-office designed restorative prosthesis can be sent from the design module 148 to the fabrication device 150 as a design file. The design file provides a digital representation of dental restorative product that is usable by a fabrication device 150 to generate the physical dental restorative product. The restorative prosthesis can be fabricated chairside using one or more of the available additive manufacturing techniques, including but not limited to stereolithography (SLA), 3D printing, and digital light processing (DLP) based, 3D printing. SLA and DLP can use a photopolymerization process, which produces a solid part (e.g., dental restorative product) from a liquid photopolymer. Other 3D printing technologies include extrusion deposition, granular materials binding, and lamination. 3D printers and materials, including but not limited to those provided by Envision TEC or DWS systems, can be used to manufacture long term temporaries. The fabrication device 150 may use any other dental manufacturing process at the dental treatment office or away from the dental treatment office. Although, the design for the dental restorative product can be realized using the fabrication device 150 located at the dental treatment office, the design for the dental restorative product may also be sent (e.g., via the Internet, other computer network to a secure server, or mail using an electronic medium) to another facility to fabricate the dental restorative product using any type of dental manufacturing process (e.g., milling machine).

Various benefits can result from using the design for the dental restorative product based on the patient's own personal 3D images. For example, the workflow used to create the design can be improved due to a reduction in the amount of time needed for the design of the final restoration, which can reduce the expected time the patient waits in the dental chair. Another benefit is improved form and fit of the final restoration by using the patient anatomy for the occlusal surface, which can help in maintaining the patient's natural bite pattern (e.g., surface to surface touch points and clearances) and thus can enhance the patient comfort or acceptance for the design. In addition to improved occlusal surfaces, prior computation of mesial and distal surface profiles and adjacent tooth clearances based on scanned patient anatomy can enhance the fit of the restoration.

Figure 2:
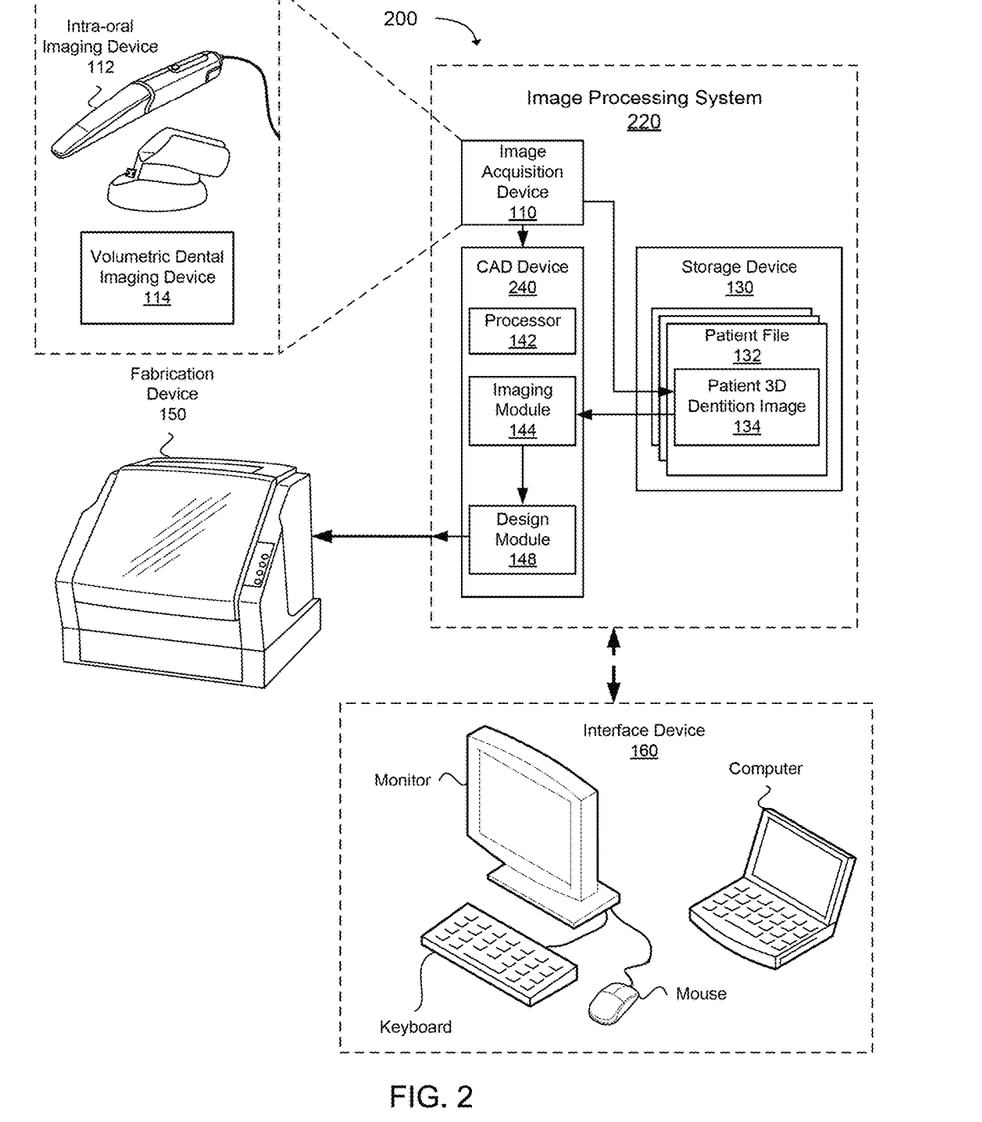
FIG. 2 illustrates a system to generate a design for a dental restorative product from a personalized library of one or more dental images of a patient.

FIG. 2 illustrates another embodiment where the patient's 3D dentition image 134 can be obtained using the image acquisition device 110 of the image processing system 220. The 3D dentition image 134 obtained prior to a change in dentition can be stored in the storage device 130 with the patient file 132. If and/or when the patient needs the dental restorative product, the 3D dentition image 134 can be obtained from the imaging module 144 and used as a basis for the design of the dental restorative product. The design module 148 can recommend an initial design based on the 3D dentition image 134 obtained prior to a change in dentition and the requested type of dental restorative product, or the dental practitioner can select the initial design based on the 3D dentition image 134. The CAD device 240 used to generate the design for the dental restorative product can include a processor 142, the imaging module 144, and the design module 148. The storage device 130 can include one or more patient files 132. Each patient file includes one or more patient 3D dentition images 134.

In one example, the dental practitioner can determine that a change in dentition has occurred and select type of dental restorative product based on a visual inspection of the patient's mouth. In another example, the image acquisition device 110 can be used to obtain a 3D dentition image 134 after a change in dentition, and the design module 148 can recommend a type of dental restorative product based on a comparison between the post-change 3D image of the patient after the change in dentition and the pre-change 3D image of the patient prior to the change in dentition. The design module 148 can generate the design for the dental restorative product based on at least one difference between the pre-change 3D image and the post-change 3D image. For example, the design module 148 can compute the volumetric shape or gap defined by the space or difference between the pre-change and post-change surfaces on one or more teeth, and can generate an initial restorative design that is shaped to fill that gap. The post-change 3D image and the pre-change 3D image are examples of the 3D dentition image 134.

Figure 4:
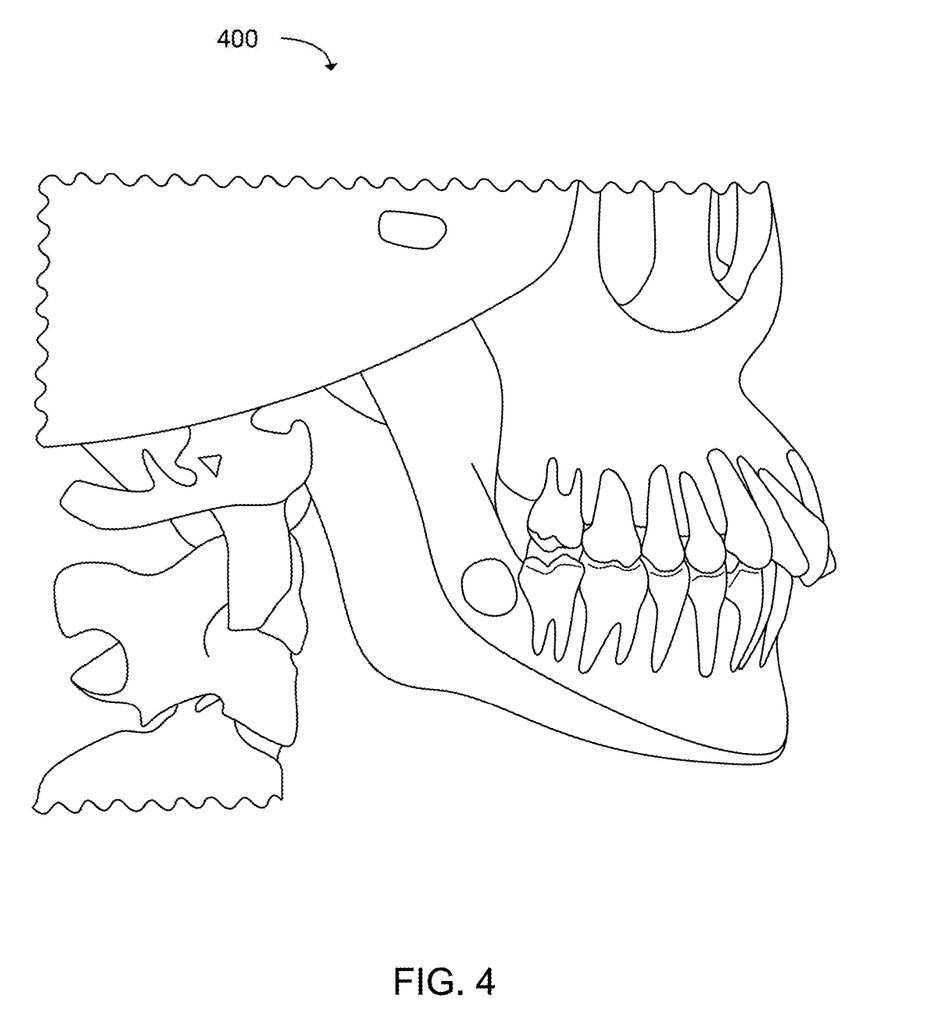
FIG. 4 illustrates volumetric imagery from a cone beam computed tomography (CBCT) scan.

In another embodiment, a volumetric dental image, including but not limited to a CBCT scan 400 of FIG. 4, can also be used to generate the design for the dental restorative product. The volumetric dental image can be obtained from a volumetric dental imaging device 114 and is another example of the patient 3D dentition image 134. For example, during volumetric dental imaging, the volumetric dental imaging device 114 (e.g., a CBCT scanner) rotates around the patient's head, obtaining multiple distinct two dimensional (2D) images. A single rotation (e.g., typically up to 200 degrees for non-offset scanning, or 360 degrees or more for offset scanning) of the volumetric dental imaging device 114 over the region of interest (e.g., the patient's head) acquires a volumetric data set that includes the multiple 2D digital images. Computing circuitry (e.g., software), the volumetric dental imaging device 114, or image processing system 120 or 220 collects the digital 2D image data, reconstructs the data, and generates a digital volume composed of three-dimensional voxels of anatomical data that can then be manipulated and visualized with the image processing system 120 or 220 (e.g., CAD/CAM system). A voxel represents a value on a regular grid in three-dimensional space. For example, the term voxel is a combination of pixel and volume.

The volumetric imagery of a patient's tooth may be received on a computational device (e.g., image processing system 120 or 220, image acquisition device 110, or CAD device 140 or 240) similar to the computational device used to process the intra-oral image. The modality for generating a volumetric image can include x-ray imaging (e.g., CBCT), MRI, or ultrasound imaging. The unreconstructed volumetric data that include multiple 2D digital images from a multidirectional scan is another example of the patient 3D dentition image 134.

Volumetric dental images and intra-oral images can show different features and can have different resolutions. For example, the intra-oral images can provide the full crown data, which can be fused with the volumetric images showing features below the crown. In addition, the intra-oral images obtained using the intra-oral imaging device (e.g., an intra-oral scanner) can have a significantly higher precision as compared with volumetric images, including but not limited to those obtained using CBCT technology. Therefore, intra-oral images alone can be adequate in the design of many dental restorative products. But, in some scenarios, the intra-oral images may not show all the features needed to generate the design of the dental restorative product. Thus, in some cases the combination of intra-oral images with volumetric images of the patient dentition or anatomy can be used to generate a better design of the dental restorative product than using the intra-oral images alone or the intra-oral image in combination with a stock design for a below the crown feature that does not account for the patient's specific dentition or anatomy.

The image processing system 120 can be used to register elements from a previously obtained intra-oral image (e.g., available from patient file 132 scanned a priori) with corresponding voxels of the volumetric image using any algorithm for combining the same features from at least two different images or types of images, including but not limited to an ICP process, a 4PCS process, some other variant of ICP or 4PCS, and/or other point set registration processes. Point set registration, also known as point matching, is the process of finding a spatial transformation that aligns two point sets into a globally consistent model. ICP is an algorithm employed to minimize the difference between two clouds of points (e.g., voxels). In the ICP algorithm, one point cloud, the reference or target, is kept fixed, while the other point cloud, the source, is estimated (e.g., using a mean squared error (MSE) function) and transformed to best match the reference. The ICP algorithm iteratively revises the transformation (combination of translation and rotation) needed to minimize the distance from the source to the reference point cloud. 4PCS is a fast and robust alignment scheme for 3D point sets that uses wide bases, which are known to be resilient to noise and outliers. The 4PCS algorithm allows registering raw noisy data, which may be contaminated with outliers, without pre-filtering or de-noising the data. 4PCS can significantly reduce the number of iterations or trials used to establish a reliable registration between the underlying surfaces in the presence of noise, without any assumptions about starting alignment. 4PCS can extract the coplanar 4-points sets from a 3D point set that are approximately congruent, under rigid transformation, to a given set of coplanar 4-points.

A benefit of combining the intra-oral imagery and the volumetric imagery can include treating a patient that has lost a complete tooth or a portion of a tooth and where the treatment plan includes an implant based artificial tooth placement at the edentulous site (i.e., toothless site or the site without the tooth). The volumetric imagery can provide details not shown in the intra-oral image. The availability of intra-oral imagery of the patient anatomy can be used by the image processing system 120 or 220 to make a recommendation of initial crown shape and size to the dental practitioner using the treatment planning software (e.g., CAD/CAM software) in the restoration design and fabrication system 100 for an integrated implant planning approach with consideration for restoration design. The intra-oral imagery may have limited usefulness if the patient has a worse than class II malocclusion at the time when the intraoral imagery was generated.

Figure 5:
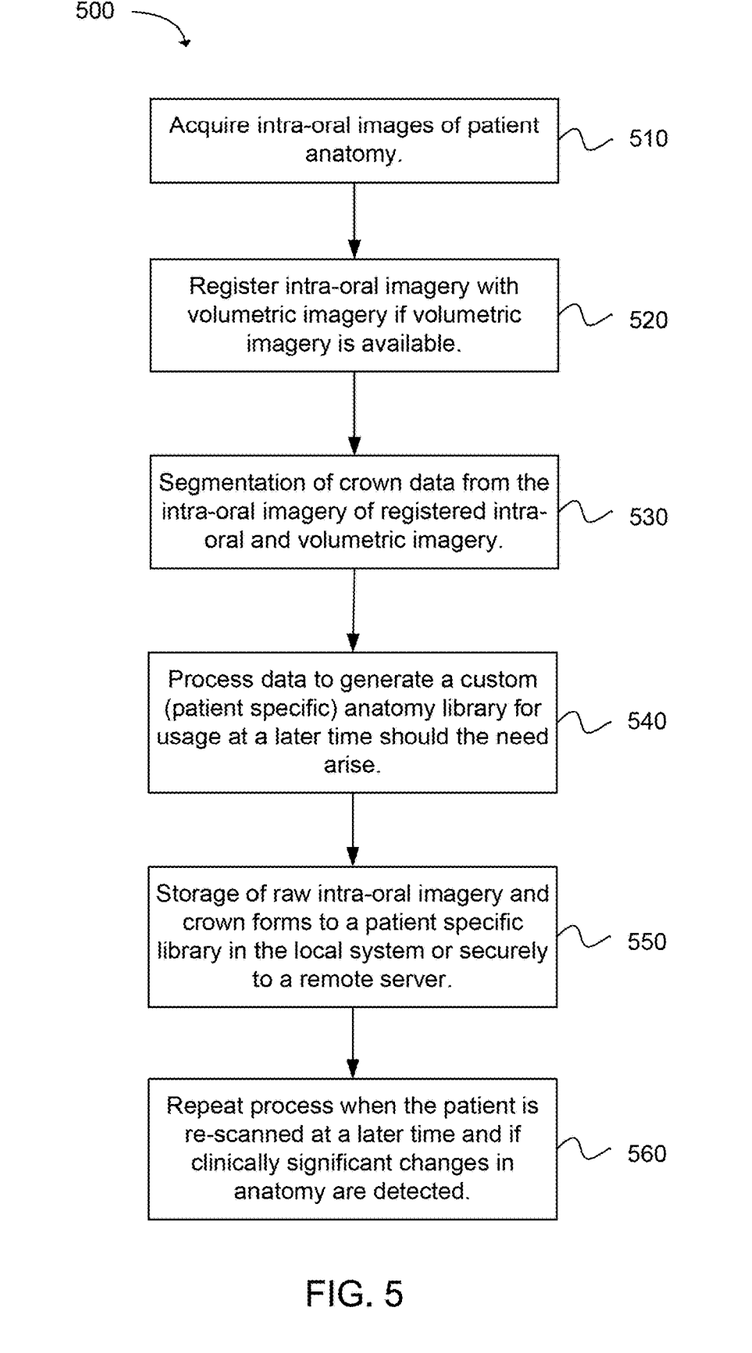
FIG. 5 is an example of a flowchart illustrating a method for creating a personalized library of one or more dental images of a patient.

FIG. 5 illustrates an example flow 500 using both intra-oral imagery and volumetric imagery. In a beginning step 510, a patient 3D dentition image 134 is the form of an intra-oral image of the patient's anatomy is acquired via the image acquisition device 110. In a next step 520, the intra-oral imagery can be registered with volumetric imagery (another patient 3D dentition image 134 previously saved or recently acquired) via the imaging module 142, if the volumetric imagery is available. If the volumetric imagery is available, the intra-oral imagery can be combined with the volumetric imagery using a point set registration process (e.g., ICP or 4PCS). In another step 530, crown data 138 can be obtained by segmenting the intra-oral imagery derived from the registered intra-oral and volumetric imagery. In a next step 540, the CAD/CAM device 140 or 240 can process the crown data 138 to generate a custom (i.e., patient specific) anatomy library for usage at a later time should the need arise. In another step 550, the original (i.e., raw) intra-oral imagery and crown data 138 can be saved in a storage device 130 (e.g., in a local computer system or securely to a remote server) to a patient specific library (e.g., patient CAD-formatted library 136) or patient file 132. In a next step 560, the process can repeat when the patient is re-scanned at a later time when or if clinically significant changes are detected in the anatomy (e.g., dentition). Then, a design file can be generated and/or a dental restorative product can be fabricated based on the intra-oral imagery and crown data 138 as previously described.

In other embodiments, the design of the dental restorative product may be generated from a 3D image of dentition based on the volumetric image alone without using an intra-oral image.

In another example, the intra-oral image (either prior to a change in dentition or after a change in dentition) can be generated from a plurality of intra-oral image using a point set registration process (e.g., ICP or 4PCS), or the volumetric image (either prior to a change in dentition or after a change in dentition) can be generated from a plurality of volumetric images using a point set registration process (e.g., ICP or 4PCS). For example, multiple intra-oral images can be obtained at different times (e.g., various check-ups). The 3D images (e.g., the intra-oral images and/or volumetric image) can be combined to generate a composite intra-oral image that represents subtle changes to dentition over time or can correct for scanning errors or noise, which can provide a more accurate 3D image. Alternatively, the latest 3D image prior to a significant change in dentition (where a dental restorative product is recommended) may be used as a basis for the design of the dental restorative product since the latest 3D image can show recent ordinary wear and tear of the dentition.

Figure 6:
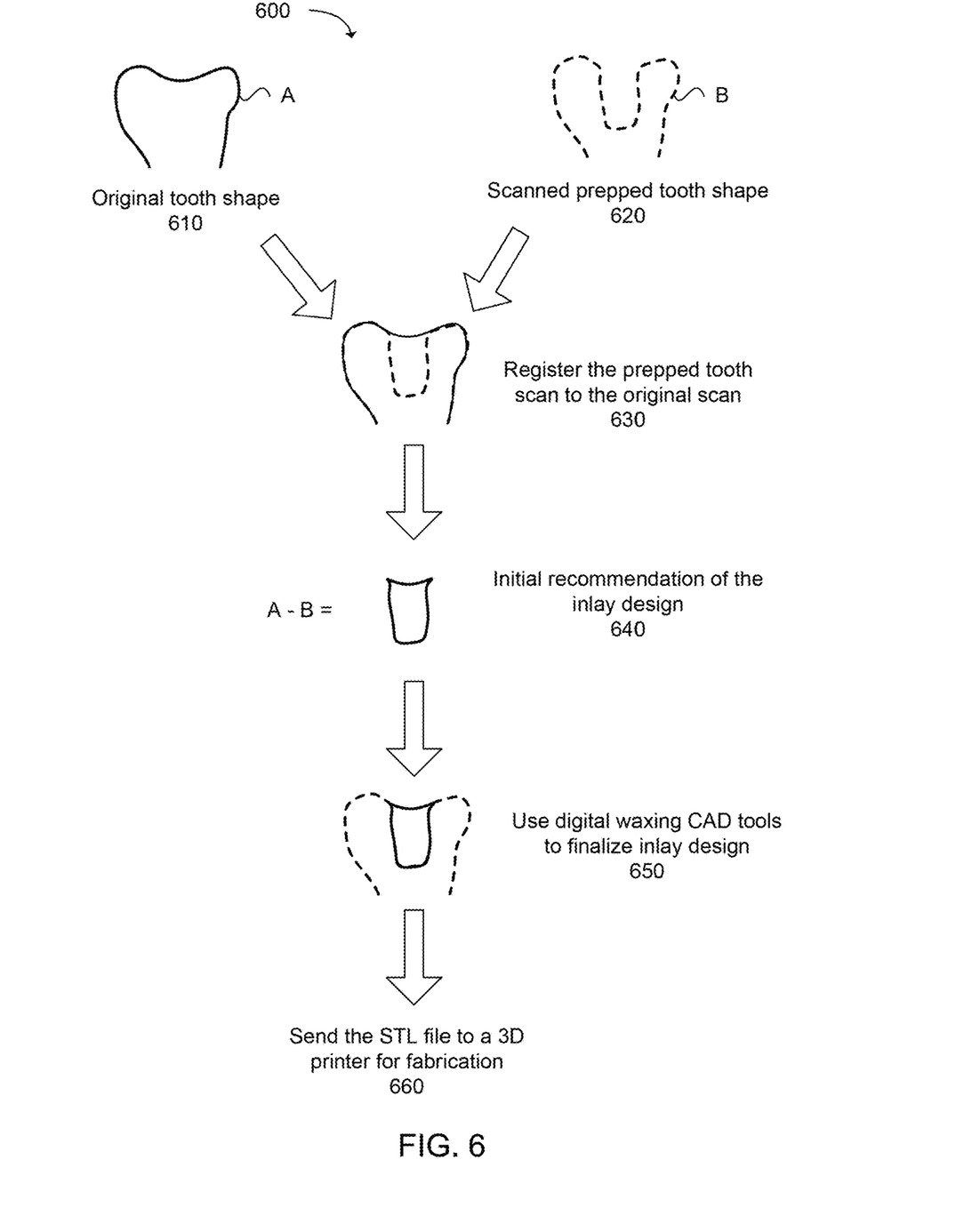
FIG. 6 is a block diagram illustrating an example of a design of an inlay using the patient specific custom anatomy library.

FIG. 6 illustrates another embodiment 600 where a 3D image (e.g., optical imagery) can be used to generate a dental restorative product (e.g., an inlay). For example, during a routine dental check-up (e.g., occurring every 2-5 years), a patient's crown data is obtained that captures the original tooth shape A using the image acquisition device 110 (e.g., an intra-oral scanner 112) as shown in step 610. The intra-oral images so obtained can be segmented via a segmenting module 146 into individual crowns and stored as digital 3D image files (e.g., STL files) in the storage device 130 of the image processing system 120. This set of digital 3D image files can provide a personalized anatomy library for the patient.

If or when the patient needs treatment (e.g., constructing an inlay), the dental practitioner can scan, using the image acquisition device 110, the specific or prepared tooth for treatment that captures the prepped tooth shape B (representing the same tooth of the patient with the saved original tooth shape scan), as shown in step 620. The specific tooth for which the inlay is to be constructed can be segmented via segmenting module 146 from the full dentition scan. This segmented tooth (e.g., prepped tooth) can then be registered or compared with the segmented digital representation of the same tooth (i.e., original tooth shape A) from the personalized anatomy library of the patient previously created using the CAD device 140, as shown in step 630. A point set registration process (e.g., 4PCS or ICP algorithm) can be used for the registration of the two data sets.

The CAD/CAM software of the image processing system 120 can then utilize the patient's own personalized anatomy library for design of the inlay to be fabricated. Boolean operations (e.g., subtraction of the 3D CAD/CAM model of the prepared tooth form from the 3D CAD/CAM model of the original healthy tooth form (i.e., A-B) to compute the volumetric shape or gap between the original tooth shape A and the post-preparation tooth shape B) can provide a near final design of the inlay with a similar occlusal surface as the patient's natural teeth, as shown in step 640. The initial design can then be modified using the tools (e.g., digital waxing tools) in the 3D CAD/CAM software as desired, as shown in step 650. Digital waxing allows a dental practitioner to fine tune a design by adding or removing material (e.g., wax) as needed. Boolean operations and/or modifications of step 650 can be performed by the design module 148.

Then the design file (e.g., STL file) for the dental restorative product can be fabricated by a fabricating device 150 (e.g., 3D printer), as shown in step 660. The fabricating device may be located at a dental treatment office (e.g., where the design is generated) or at another location away from the dental treatment office. The fabrication device 150 can use a milling machine or an additive manufacturing device where the additive manufacturing device uses an additive manufacturing technique, including but not limited to stereolithography, 3D printing, or DLP based, 3D printing. In another example, the method 600 of FIG. 6 can be carried out using other hardware and/or components of the restoration design and fabrication system 100 as well.

Figure 7:
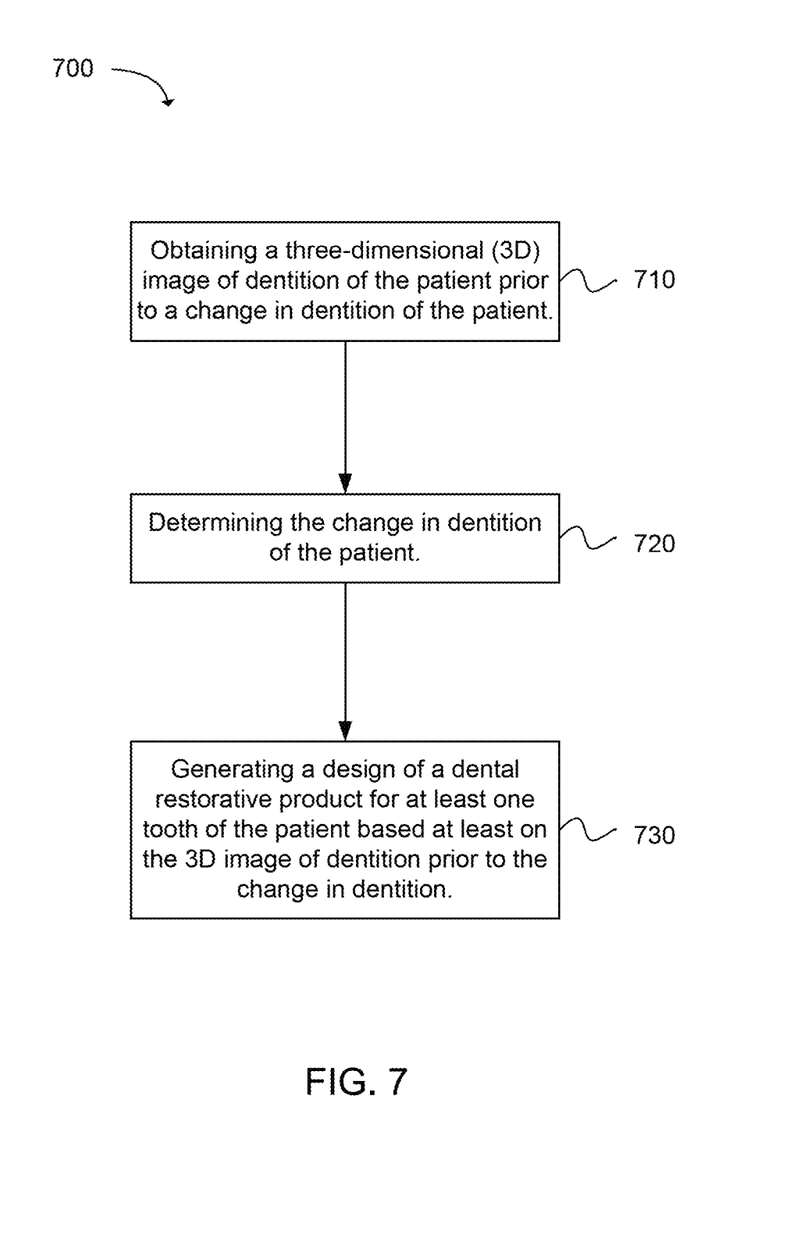
FIG. 7 is flowchart illustrating an example of a method for generating a design for a dental restorative product from one or more dental images of a patient.

Another example provides a method 700 for generating a design for a dental restorative product from one or more dental images of a patient, as shown in the flow chart in FIG. 7. The method includes the step of obtaining a 3D image of dentition of the patient prior to a change in dentition of the patient, as in step 710. The step of determining the change in dentition of the patient follows, as in step 720. The next step of the method is automatically generating a design of a dental restorative product for at least one tooth of the patient based at least on the 3D image of dentition prior to the change in dentition, as in step 730.

In another example, the method can further include sending the design in the form of a design file to a fabrication device and then fabricating the dental restorative product based on the design file, as previously described.

Various techniques, or certain aspects or portions thereof, may take the form of program code (i.e., instructions) embodied in tangible media, including but not limited to floppy diskettes, compact disc-read-only memory (CD-ROMs), hard drives, non-transitory computer readable storage medium, or any other machine-readable storage medium where the program code is loaded into and executed by a machine (e.g., a computer) the machine becomes an apparatus for practicing the various techniques. Circuitry (e.g., computing circuitry) can include hardware, firmware, program code, executable code, computer instructions, and/or software. A non-transitory computer readable storage medium can be a computer readable storage medium that does not include signal. In the case of program code executing on programmable computers, the computing device may include a processor, a storage medium readable by the processor (including volatile and non-volatile memory and/ or storage elements), at least one input device, and at least one output device. The volatile and non-volatile memory and/or storage elements may be a random-access memory (RAM), erasable programmable read only memory (EPROM), flash drive, optical drive, magnetic hard drive, solid state drive, or other medium for storing electronic data. One or more programs that may implement or utilize the various techniques described herein may use an application programming interface (API), reusable controls, and the like. Such programs may be implemented in a high level procedural or object oriented programming language to communicate with a computer system. However, the program(s) may be implemented in assembly or machine language, if desired. In any case, the language may be a compiled or interpreted language, and combined with hardware implementations.

It should be understood that many of the functional units described in this specification have been labeled as modules, in order to more particularly emphasize their implementation independence. For example, a module may be implemented as a hardware circuit comprising custom very-large-scale integration (VLSI) circuits or gate arrays, off-the-shelf semiconductors, including but not limited to logic chips, transistors, or other discrete components. A module may also be implemented in programmable hardware devices, including but not limited to field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executable code of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

Reference throughout this specification to "an example" or "exemplary" means that a particular feature, structure, or characteristic described in connection with the example is included in at least one embodiment of the present invention. Thus, appearances of the phrases "in an example" or the word "exemplary" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided (e.g., examples of layouts, distances, network examples) to provide a thorough understanding of embodiments of the invention. One skilled in the relevant art will recognize, however, that the invention can be practiced without one or more of the specific details, or with other methods, components, layouts, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A method of generating a design for a dental restorative product from one or more dental images of a patient, comprising:
    obtaining a pre-trauma three-dimensional (3D) image of dentition of the patient prior to trauma to dentition of the patient;
    obtaining a post-trauma 3D image of dentition of the patient after trauma to the dentition of the patient;
    automatically generating, by a processor, a dental restorative product file containing the design of the dental restorative product for at least one tooth of the patient based on at least one difference between the pre-trauma 3D image of dentition of the patient and the post-trauma 3D image of dentition of the patient; and
    fabricating the dental restorative product based on the design;
    wherein the dental restorative product file includes tooth tissue present in the pre-trauma 3D image of dentition but missing in the post-trauma 3D image of dentition.

2. The method of claim 1, wherein fabricating the dental restorative product further comprises: sending the design to a fabrication device including at least one selected from the group consisting of a milling machine and an additive manufacturing device, wherein the step of obtaining a pre-trauma 3D image of dentition of the patient is performed in a dental treatment office, and wherein the fabrication device is located in the dental treatment office; and
    fabricating the dental restorative product using the fabrication device based on the design.

3. The method of claim 2, wherein the additive manufacturing device uses at least one selected from the group consisting of stereolithography and digital light processing.

4. The method of claim 1, wherein obtaining the pre-trauma 3D image of dentition of the patient comprises acquiring the pre-trauma 3D image of dentition from an imaging device comprising at least one selected from the group consisting of an intra-oral imaging device and a volumetric dental imaging device.

5. The method of claim 1, wherein obtaining the pre-trauma 3D image of dentition of the patient further comprises:
acquiring an intra-oral image of the patient using a non-ionizing scanner wherein the intra-oral image includes a surface geometry file and the non-ionizing scanner includes at least one selected from the group consisting of an optical scanner and a laser scanner; or
acquiring a volumetric dental image of the patient using at least one selected from the group consisting of x-ray computed tomography, magnetic resonance imaging (MM), and ultrasound imaging.

6. The method of claim 1, obtaining the pre-trauma 3D image of dentition of the patient further comprises: acquiring an intra-oral image of the patient using a non-ionizing imaging device; determining a crown surface for a tooth above a periodontium based on the intra-oral image;
acquiring a volumetric dental image of the patient using an x-ray-based imaging device;
determining a geometry of the tooth tissue for the tooth including at least a portion of root tissue surrounded by the periodontium based on the volumetric dental image; and
generating the pre-trauma 3D image of dentition including the crown surface and at least a portion of the root tissue based on a combination of the intra-oral image and the volumetric dental image using an image registration process.

7. The method of claim 1, wherein:
the design comprises at least one selected from the group consisting of a computer-aided design-format (CAD-format) file and an image file; and
the dental restorative product comprises at least one selected from the group consisting of a dental prosthesis, a denture, an implant, an inlay, a filling, a plug, a crown, an onlay, and a veneer.

8. The method of claim 1, further comprising:
storing, in a data storage device, the pre-trauma 3D image of dentition of the patient in a personalized library associated with the patient.

9. The method of claim 1, further comprising:
segmenting the pre-trauma 3D image of dentition of the patient to generate crown data of a tooth; processing the crown data to generate a crown design file; and
storing the crown design file in a personalized library associated with the patient.

10. The method of claim 9, wherein the generating step further comprises:
obtaining the crown design file from the personalized library; and
generating the design of the dental restorative product based on the crown design file.

11. The method of claim 9, wherein:
obtaining a pre-trauma 3D image of dentition of the patient further comprises obtaining a pre-trauma design file previously saved in a personalized library of a data storage device prior to damage occurring to a tooth;
obtaining a post-trauma 3D image of dentition of the patient further comprises obtaining a post-trauma design file saved in the personalized library after damage has occurred to the tooth; and
automatically generating, by a processor, a dental restorative product file further comprises:
comparing the pre-trauma design file and the post-trauma design file for the tooth; and
generating the dental restorative product file based on a comparison between the pre-trauma design file and the post-trauma design file.

12. The method of claim 9, wherein segmenting the pre-trauma 3D image of dentition of the patient further comprises:
differentiating between the tooth tissue and non-tooth tissue in the pre-trauma 3D image of dentition; and
generating the crown data of the tooth based on the tooth tissue in the pre-trauma 3D image of dentition.

13. The method of claim 1, further comprising preparing a tooth for restoration after the step of obtaining a pre-trauma three-dimensional image of dentition of the, and wherein the post-trauma 3D image is a 3D image of dentition of the patient after the preparing step.

14. At least one non-transitory machine readable storage medium comprising a plurality of instructions adapted to be executed to implement the method of claim 1.

15. A dental computer-aided design (CAD) system configured to generate a design for a dental restorative product from one or more dental images of a patient, having computing circuitry configured to:
obtain a pre-trauma three-dimensional (3D) image of dentition of the patient prior to trauma to dentition of the patient;
obtain a post-trauma 3D image of dentition of the patient after trauma to the dentition of the patient; and
automatically generate a dental restorative product file containing the design of the dental restorative product for at least one tooth of the patient based on at least one difference between the pre-trauma 3D image of dentition of the patient and the post-trauma 3D image of dentition of the patient; and
fabricate the dental restorative product based on the design;
wherein the dental restorative product file includes tooth tissue present in the pre-trauma 3D image of dentition but missing in the post-trauma 3D image of dentition.

16. The computing circuitry of claim 15, further configured to:
acquire the pre-trauma 3D image of dentition from an imaging device comprising at least one selected from the group consisting of an intra-oral imaging device and a volumetric dental imaging device.

17. A system operable to generate a design for a dental restorative product from one or more dental images of a patient, comprising:
an imaging module configured to
obtain a pre-trauma three-dimensional (3D) image of dentition of the patient prior to trauma to dentition of the patient; and
obtain a post-trauma 3D image of dentition of the patient after trauma to the dentition of the patient;
a design module configured to:
automatically generate a dental restorative product file containing the design of the dental restorative product for at least one tooth of the patient based on at least one difference between the pre-trauma 3D image of dentition of the patient and the post-trauma 3D image of dentition of the patient;
wherein the dental restorative product file includes tooth tissue present in the pre-trauma 3D image of dentition but missing in the post-trauma 3D image of dentition; and
a fabrication device configured to fabricate the dental restorative product based on the design.

18. The system of claim 17, further comprising:
the fabrication device comprising at least one selected from the group consisting of a milling machine and an additive manufacturing device.

19. The system of claim 17, further comprising:
an image acquisition device comprising at least one selected from the group consisting of an intra-oral imaging device and a volumetric dental imaging device, the image acquisition device configured to acquire the pre-trauma 3D image of dentition.

20. The system of claim 17, further comprising:
a storage device configured to store the pre-trauma 3D image of dentition of the patient prior to trauma to dentition in a personalized library associated with the patient.

* * * * *